(12) United States Patent
Nyan et al.

(10) Patent No.: US 8,260,570 B2
(45) Date of Patent: Sep. 4, 2012

(54) METHOD AND SYSTEM FOR FALL-ONSET DETECTION

(75) Inventors: Myo Naing Nyan, Singapore (SG); Eng Hock Francis Tay, Singapore (SG); Euan Murugasu, Singapore (SG)

(73) Assignees: National University of Singapore, Singapore (SG); Singapore General Hospital, Singapore (SG)

( * ) Notice: Subject to any disclaimer, the term of this patent is extended or adjusted under 35 U.S.C. 154(b) by 383 days.

(21) Appl. No.: 12/523,808

(22) PCT Filed: Jan. 22, 2008

(86) PCT No.: PCT/SG2008/000027
§ 371 (c)(1),
(2), (4) Date: Dec. 29, 2009

(87) PCT Pub. No.: WO2008/091227
PCT Pub. Date: Jul. 31, 2008

(65) Prior Publication Data
US 2010/0121603 A1 May 13, 2010

Related U.S. Application Data

(60) Provisional application No. 60/885,956, filed on Jan. 22, 2007.

(51) Int. Cl.
*G01C 22/00* (2006.01)
(52) U.S. Cl. .................................................... 702/160
(58) Field of Classification Search .................. 702/160
See application file for complete search history.

(56) References Cited

U.S. PATENT DOCUMENTS

| | | | |
|---|---|---|---|
| 6,433,690 B2 | 8/2002 | Petelenz et al. | |
| 6,611,783 B2 | 8/2003 | Kelly, Jr. et al. | |
| 6,834,436 B2 | 12/2004 | Townsend et al. | |
| 6,871,413 B1 | 3/2005 | Arms et al. | |
| 6,915,230 B2 * | 7/2005 | Kawai et al. | 702/139 |
| 7,095,331 B2 | 8/2006 | Lehrman et al. | |
| 7,145,461 B2 | 12/2006 | Lehrman et al. | |
| 2001/0004234 A1 | 6/2001 | Petelenz et al. | |
| 2003/0058341 A1 | 3/2003 | Brodsky et al. | |

(Continued)

FOREIGN PATENT DOCUMENTS
FR 2808609 A1 11/2001
(Continued)

OTHER PUBLICATIONS

Tinetti, Mary E., M.D. "Preventing Falls in Elderly Persons" The New England Journal of Medicine, Jan. 2, 2003, pp. 42-49.

(Continued)

*Primary Examiner* — Aditya Bhat
(74) *Attorney, Agent, or Firm* — Volpe and Koenig, P.C.

(57) ABSTRACT

A method and system for fall-onset detection is provided. The method includes the steps of monitoring acceleration at the thigh of a person; monitoring acceleration at the waist of the person; monitoring orientation of the thigh of the person; and detecting the fall-onset if the orientation of the thigh exceeds a first threshold value and a correlation between variation in acceleration of the thigh and variation in acceleration of the waist exceeds a second threshold value and a correlation between variation in the orientation of the thigh and a fall-template variation exceeds a third threshold value.

15 Claims, 8 Drawing Sheets

Thigh and waist sensor sets 102, 112

U.S. PATENT DOCUMENTS

| | | |
|---|---|---|
| 2006/0001545 A1 | 1/2006 | Wolf |
| 2006/0049950 A1 | 3/2006 | Lockhart |
| 2006/0139166 A1 | 6/2006 | Choutier et al. |
| 2006/0145874 A1 | 7/2006 | Fredriksson et al. |
| 2006/0214806 A1 | 9/2006 | Clifford et al. |
| 2006/0279426 A1 | 12/2006 | Bonnet et al. |

FOREIGN PATENT DOCUMENTS

| | | |
|---|---|---|
| GB | 2323196 A | 9/1998 |
| GB | 2409321 A | 6/2005 |
| WO | 8807350 A1 | 10/1988 |
| WO | 2006080225 A1 | 8/2006 |

OTHER PUBLICATIONS

Wu, GE "Distinguishing Fall Activities From Normal Activities by Velocity Characteristics" Journal of Biomechanics 33 (2000), pp. 1497-1500.

Gillespie, Lesley "Preventing Falls in Elderly People" BMJ vol. 328, Mar. 20, 2004, pp. 653-654.

Nyan, M.N.; Tay, F.E.H.; Tan, A.W.Y; and Seah, K.H.W. "Distinguishing Fall Activities From Normal Activities by Angular Rate Characteristics and High-Speed Camera Characterization" Medical Engineering & Physics 28 (2006) pp. 842-849.

Tinetti, Mary E. M.D., et al. "Risk Factors for Falls Among Elderly Persons Living in the Community" The New England Journal of Medicine, Dec. 29, 1988, vol. 319, No. 26, pp. 1701-1707.

Tinetti, Mary E. et al. "A Multifactorial Intervention to Reduce the Risk of Falling Among Elderly People Living in the Community" The New England Journal of Medicine, Sep. 29, 1994, vol. 331, pp. 821-827.

McIntosh, Shona et al. Outcome of an Integrated Approach to the Investigation of Dizziness, Falls and Syncope in Elderly Patients Referred to a 'Syncope' Clinic Age and Aging, 1993, vol. 22, pp. 53-58.

Tinetti, Mary, E., M.D. and Speechley, Mark, Ph.D. "Prevention of Falls Among the Elderly" The New England Journal of Medicine, Apr. 20, 1989, vol. 320, No. 16, pp. 1055-1059.

"Unexplained Falls in Elderly Adults Could Be Related to Treatable Heart Condition" Doctor's Guide, Nov. 2, 2001, pp. 1-2 http://www.pslgroup.com/dg/20C942.htm.

* cited by examiner

Fig. 3(g) Fall templates

METHOD AND SYSTEM FOR FALL-ONSET DETECTION

FIELD OF INVENTION

The present invention relates broadly to a method and system of fall-onset detection.

BACKGROUND

Falls and fall-related injuries are the most common cause of injuries and hospital admissions for trauma among the elderly. Among the causes of falls, fainting (syncope) is one important factor in older people and also related often to unexplained and recurrent falls. In these circumstances, a wearable system competent in faint fall onset detection will offer great advantages to elderly health care in terms of reducing elderly health care expenditure, and helping elderly with fall experiences rehabilitate, regain confidence and independence in free living conditions.

In Ge Wu, "Distinguishing fall activities from normal activities by velocity characteristics", Journal of Biomechanics 2000; 33(11) 1497-1500, detection of falls before the subjects touches the floor using cameras is described. Other fall incidents detection systems using camera or motion sensors are proposed in e.g. US2006145874, GB20052409321, US2003058341, US2001004234, FR20012808609, US2006214806, WO2006080225, US20067095331, US20036611783, WO198800007350. US20060001545A1 and US2006049950 propose detection of fall before touching the floor using accelerometers. A threshold level for vertical acceleration, 8 m/square sec, is set which is alleged to distinguish fall from normal activity. However, in order to detect a vertical acceleration of 8 m/square sec, practically the person would have to undergo a more than 45° rotation from the vertical axis. Therefore, in this scenario the fall has already significantly progressed before detection is possible.

A need therefore exist to provide a system and method for fall on set detection that seeks to address one or more of the above disadvantages.

SUMMARY

In accordance with a first aspect of the present invention there is provided a method of fall-onset detection, the method comprising the steps of monitoring acceleration at the thigh of a person; monitoring acceleration at the waist of the person; monitoring orientation of the thigh of the person; and detecting the fall-onset if the orientation of the thigh exceeds a first threshold value and a correlation between variation in acceleration of the thigh and variation in acceleration of the waist exceeds a second threshold value and a correlation between variation in the orientation of the thigh and a fall-template variation exceeds a third threshold value.

The first threshold value may be about ±10°.

The second threshold value may be about 0.88.

The third threshold value may be 0.8.

The acceleration of the thigh may be monitored three-dimensionally as $\{x_{TS}$: vertical (downward positive); $y_{TS}$: lateral (right positive); $z_{TS}$: sagittal (forward positive)$\}$ The acceleration of the waist may be monitored three-dimensionally as $\{x_{WS}$: vertical (downward positive); $y_{WS}$: lateral (right positive); $z_{WS}$: sagittal (forward positive)$\}$ The orientation of the thigh may be measured two-dimensionally as lateral (left positive) and sagittal (back positive) directions.

The monitored acceleration of the thigh and waist may be transformed into two-dimensional body orientation and the correlation between the variation in acceleration of the thigh and variation in acceleration of the waist may be determined with regard to the transformed two-dimensional body orientation.

The monitored acceleration of the thigh and waist may be transformed into two-dimensional body orientation $\deg_{SAG}$, $\deg_{LAT}$, as:

$$\deg_{SAG} = -a\tan(z_{TSorWS}/x_{TSorWS})*(180/\mathrm{pi}),$$

$$e = \mathrm{sqrt}(1-(y_{TSorWS}*y_{TSorWS})), \text{ and}$$

$$\deg_{LAT} = a\tan(y_{TSorWS}/e)*(180/\mathrm{pi}).$$

The correlation between variation in acceleration of the thigh and variation in acceleration of the waist may be determined over a first data segment of pre-determined sample length.

The sample length is about 20.

The correlation between variation in the orientation of the thigh and a fall-template variation may be determined over a second data segment of pre-determined sample length.

The sample length may be about 80.

The method may further comprise performing a feedback step in response to the fall-onset detection.

In accordance with a second aspect of the present invention there is provided a system for fall-onset detection, the system comprising a first accelerometer for monitoring acceleration at the thigh of a person; a second accelerometer for monitoring acceleration at the waist of the person; a gyroscope for monitoring orientation of the thigh of the person; and a processor coupled to the first and second accelerometers and to the gyroscope for detecting the fall-onset, the processor being operable to detect the fall-onset based if the orientation of the thigh exceeds a first threshold value and a correlation between variation in acceleration of the thigh and variation in acceleration of the waist exceeds a second threshold value and a correlation between variation in the orientation of the thigh and a fall-template variation exceeds a third threshold value.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

The described embodiment provides a wearable real-time system that can distinguish between faint falls versus normal bodily activities at their onset stages. Upon detection of the onset, as a consequence, another feedback system can be deployed during the lead time in preventing the fall or reducing the severity of fall related injuries.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "calculating", "determining", "generating", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The invention may also be implemented as hardware modules. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

The described embodiment exploits, interalia, a premise that the thigh segment does not go beyond certain threshold angle in forward and sideways directions in normal activities and this abnormal behavior occurs in faint falls for faint fall onset detection.

Figure 1A:
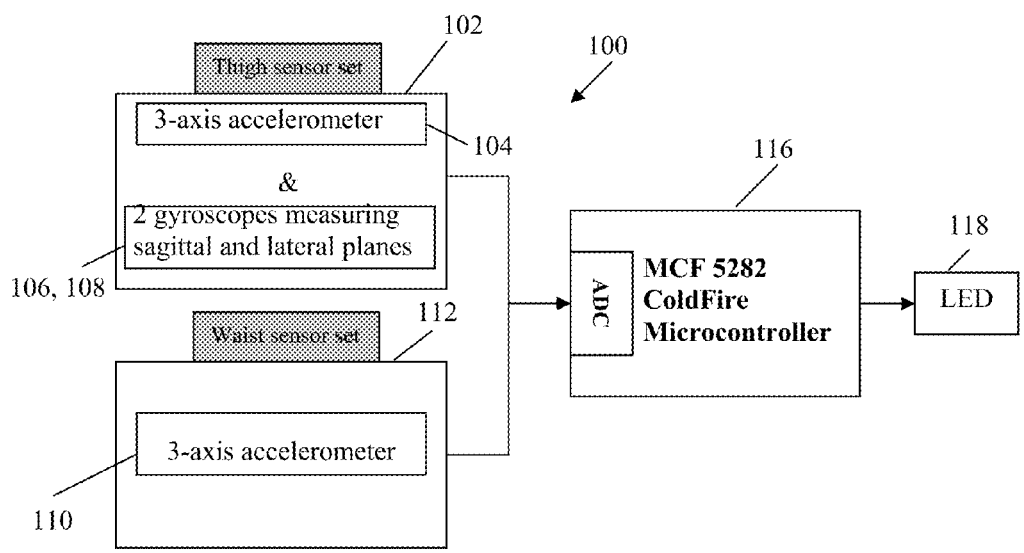
FIGS. 1a and b show a schematic diagram and a photo respectively of a system for fall-onset detection according to the example embodiment.
Figure 1B:
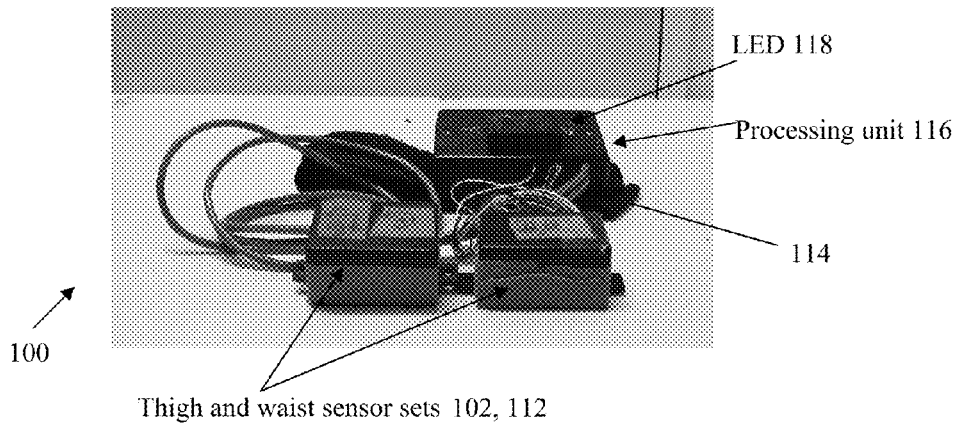

A hardware setup 100 of the embodiment is shown in FIGS. 1a and b. A thigh sensor set (TS) 102 contains one MMA7260Q (±4 g, 300 mV/g) three axis micromachined accelerometer 104 {x: vertical (downward positive); y: lateral (right positive); z: sagittal (forward positive)} and two ADXRS150 (±150°/sec) yaw rate gyroscopes 106, 108 measuring in lateral (left positive) and sagittal (back positive) directions. One three axis accelerometer 110 is included in a waist sensor set (WS) 112 with similar sensitivity axis setting as that in TS 102. WS and TS 112, 102 are attached using Velcro 114 at the front of the waist and at the front, slightly above mid level, of the thigh. Eight channels of sensor data are sampled at 47 samples/sec rate into the MCF5282 Cold-Fire microcontroller 116 for data processing. An LED 118 will light up upon detection of the onset of fall.

Microcontroller 116 may be connectable to a computer network via a suitable transceiver device, to enable access to e.g. the Internet or other network systems such as Local Area Network (LAN) or Wide Area Network (WAN). The Microcontroller 116 in the example includes a processor, a Random Access Memory (RAM) and a Read Only Memory (ROM).

The Microcontroller 116 also includes a number of Input/Output (I/O) interfaces. The components of the Microcontroller 116 typically communicate via an interconnected bus and in a manner known to the person skilled in the relevant art. The application program for the Microcontroller 116 is typically encoded on the RAM of the Microcontroller 116. The application program is read and controlled in its execution by the processor.

Figure 2:
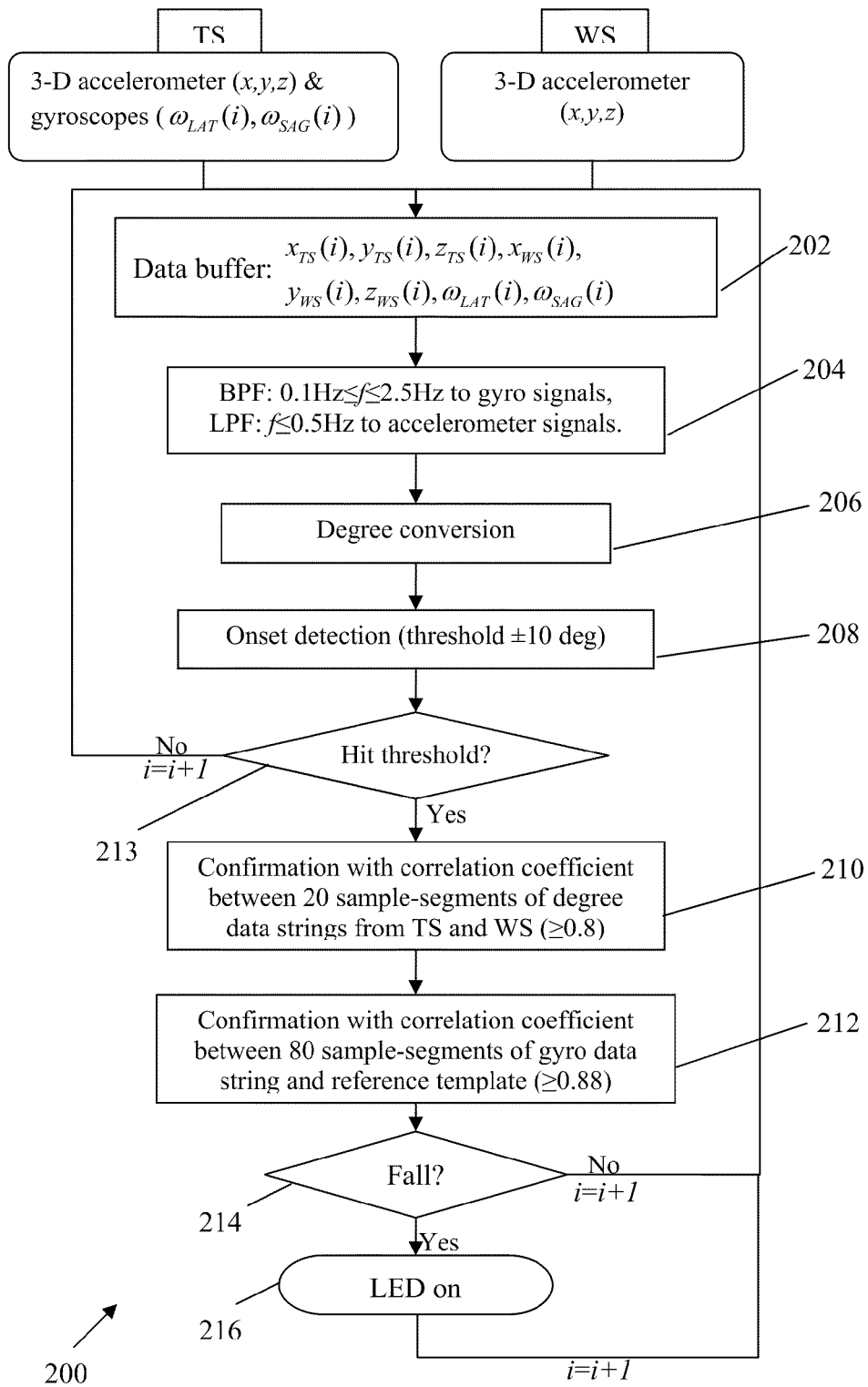
FIG. 2 shows a flow chart illustrating a method for fall-onset detection according to the example embodiment.

FIG. 2 shows the process flow 200 of the onset detection algorithm in the example embodiment. The $i^{th}$ sample of the accelerometers ($x_{TS}(i)$, $y_{TS}(i)$, $z_{TS}(i)$, $x_{WS}(i)$, $y_{WS}(i)$, $z_{WS}(i)$) stored as buffered data at step 202, are low pass filtered with a cutoff frequency less than and equal to 0.5 Hz at step 204 and the $i^{th}$ sample of the gyroscopes ($\omega_{LAT}(i)$, $\omega_{SAG}(i)$) stored as buffered data at step 202, are band a pass filtered with pass band between 0.01 Hz and 2.5 Hz at step 204. Fainite Impulse Response (FIR) filters are used in filtration in the example embodiment. Next, the acceleration samples are transformed into two dimensional degrees of body orientation at step 206, measuring how many degrees these body segments are deviated from the vertical axis, e.g., standing is zero degree and lying flat on the floor is ninety degree, using the following equations, $$\deg_{SAG(TSorWS)} = -a\tan(z_{TSorWS}/x_{TSorWS})*(180/pi),$$

$$e = \sqrt{1-(y_{TSorWS}*y_{TSorWS})}, \text{ and}$$

$$\deg_{LAT(TSorWS)} = a\tan(y_{TSorWS}/e)*(180/pi).$$

If $\deg_{SAG}$ (positive for backward rotation) or $\deg_{LAT}$ (positive for left side rotation) hits the threshold value ±10 deg at step 208, fall is confirmed at steps 210 and 212 with correlation coefficient ($\rho_{deg} \geq 0.8$) of two angle data segments, {$\deg_{TS}(-N+i)$; $i=0, \ldots, N$ and $N=19$} and {$\deg_{WS}(-N+i)$; $i=0, \ldots, N$ and $N=19$}, where deg(0) is the detected point of onset, from two sensor sets at step 210, and the correlation ($\rho_\omega \geq 0.88$) between the band pass filtered gyroscope segment {$\omega(-N+i)$; $i=0, \ldots, N$ and $N=79$}, where $\omega(0)$ is the detected point of onset, and its corresponding reference template (step 212). Here, the word "corresponding" is to be understood as that detected positive lateral/sagittal degree sample is correlated with left/backward a fall reference template and detected negative sample involves correlation with a right/forward fall reference template.

In the example embodiment, separate correlations for lateral (LAT) and sagittal (SAG) rotational movements are calculated, i.e. between $\deg_{LAT\,TS}$ and $\deg_{LAT\,WS}$ on the one hand, and between $\deg_{SAG\,(TS)}$ and $\deg_{SAG\,(WS)}$.

The LED (118, FIG. 1a) will be on if the coefficients $\rho_{deg}$, $\rho_\omega$ are simultaneously above or equal to 0.8 and 0.88 respectively. In this detection, only the thigh degree samples traveling from 0 to ±90 degree, as the thigh rotates from 0 to ±90 degree in fall activities, are taken as points of interest for the confirmation process in the example embodiment, by measuring the slope of the sample as (($\deg_i - \deg_{i-5}$)/5), where $\deg_i$ is equal to ±10 degree. The whole algorithm for the $i^{th}$ samples are completed within 21 msec sampling interval before the next $i+1^{th}$ sample is taken in. Compared to using integrated gyroscope outputs in measuring thigh angle segment rotation from vertical axis, integration errors caused by noise and offset resulting in integrated values, which easily passing through the ±10 degree threshold level even if the subject is still, can be avoided in the example embodiment.

The process loops back at either the "NO" decisions at steps 213 or 214, or after the LED (118, FIG. 1a) has been maintained or turned on at step 216, to the next sample in the data buffer at step 202.

In the example embodiment, false alarm arising from movement of thigh in stand-sit transition, similar to backward fall, can be easily identified and rejected by means of low a correlation coefficient resulting from opposite movements of thigh and trunk in such activity (compare steps 210, 212).

Figure 3A:
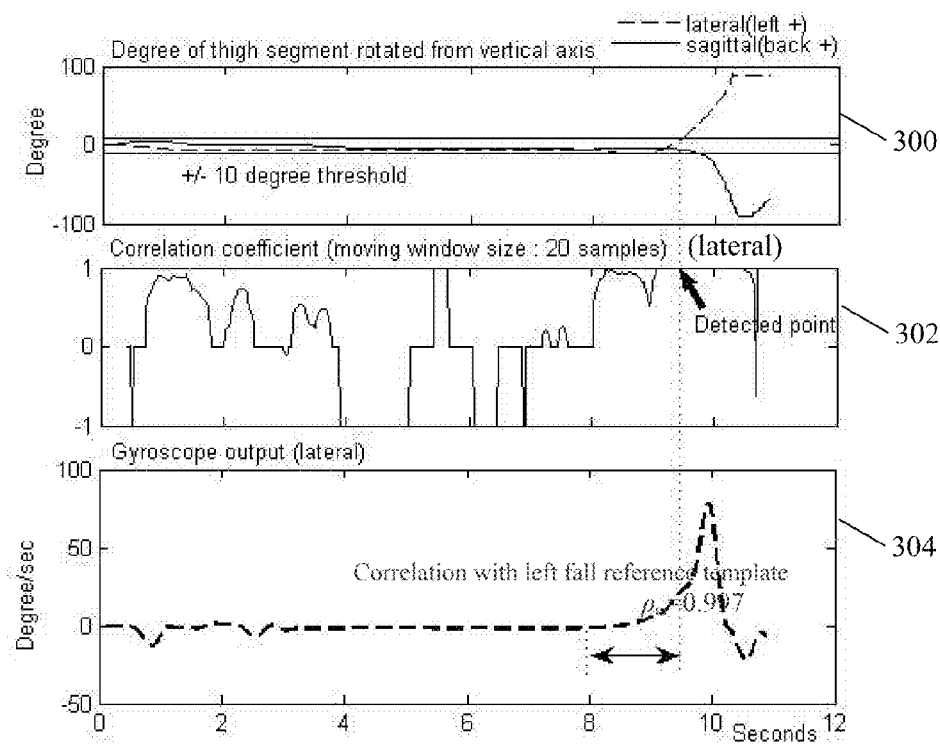
FIG. 3a to d show measurement graphs of the method and system for fall-onset detection according to the example embodiment for different respective fall scenarios.

FIG. 3a shows thigh angle rotation from vertical axis (graph 300), the correlation coefficient of the angle data segments from TS and WS (graph 302), the gyroscope output (graph 304), and the correlation coefficient (indicated in graph 304) of the band pass filtered output of an eighty samples long segment and its corresponding reference template for a simulated left side fall for a simulated left side fall. High correlation coefficients of $\rho_{deg}$ and $\rho_\omega$ can be seen in the fall activity.

Figure 3B:
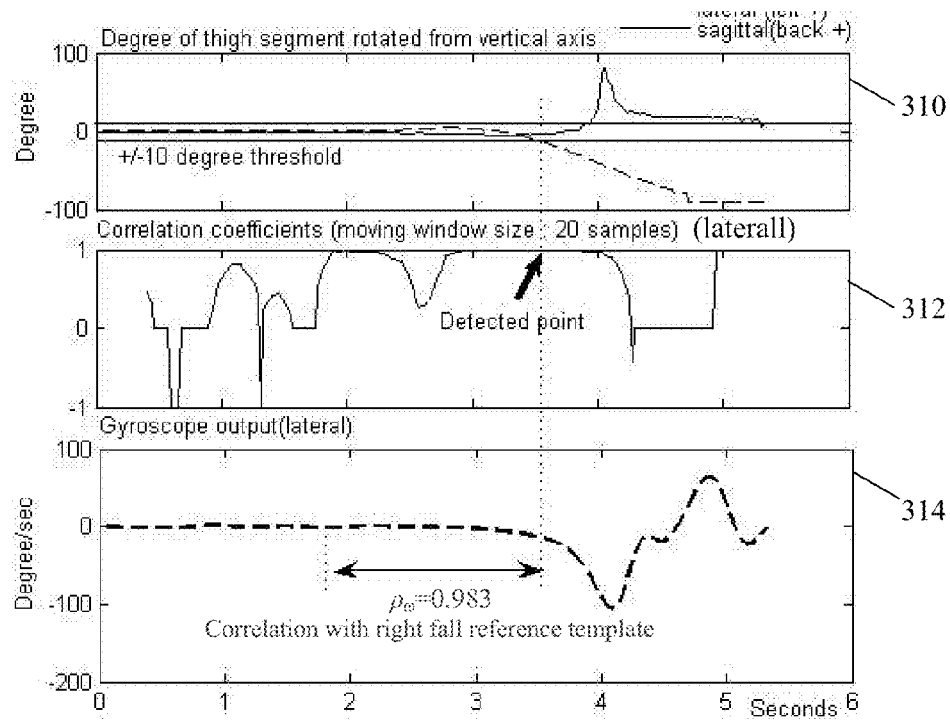

FIG. 3b shows thigh angle rotation from vertical axis (graph 310), the correlation coefficient of the angle data segments from TS and WS (graph 312), the gyroscope output (graph 314), and the correlation coefficient (indicated in graph 314) of the band pass filtered output of an eighty samples long segment and its corresponding reference template for a simulated left side fall for a simulated right side fall. High correlation coefficients of $\rho_{deg}$ and $\rho_\omega$ can be seen in the fall activity.

Figure 3C:
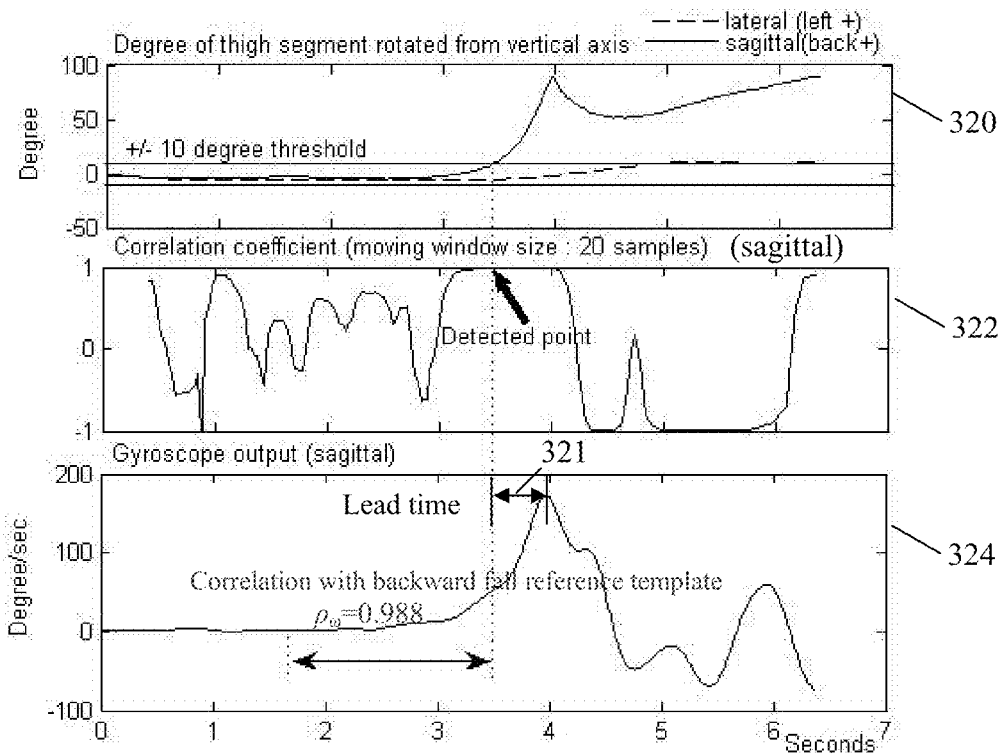

FIG. 3c shows thigh angle rotation from vertical axis (graph 320), the correlation coefficient of the angle data segments from TS and WS (graph 322), the gyroscope output (graph 324), and the correlation coefficient (indicated in graph 324) of the band pass filtered output of an eighty samples long segment and its corresponding reference template for a simulated left side fall for a simulated backward fall. High correlation coefficients of $\rho_{deg}$ and $\rho_\omega$ can be seen in the fall activity.

Figure 3D:
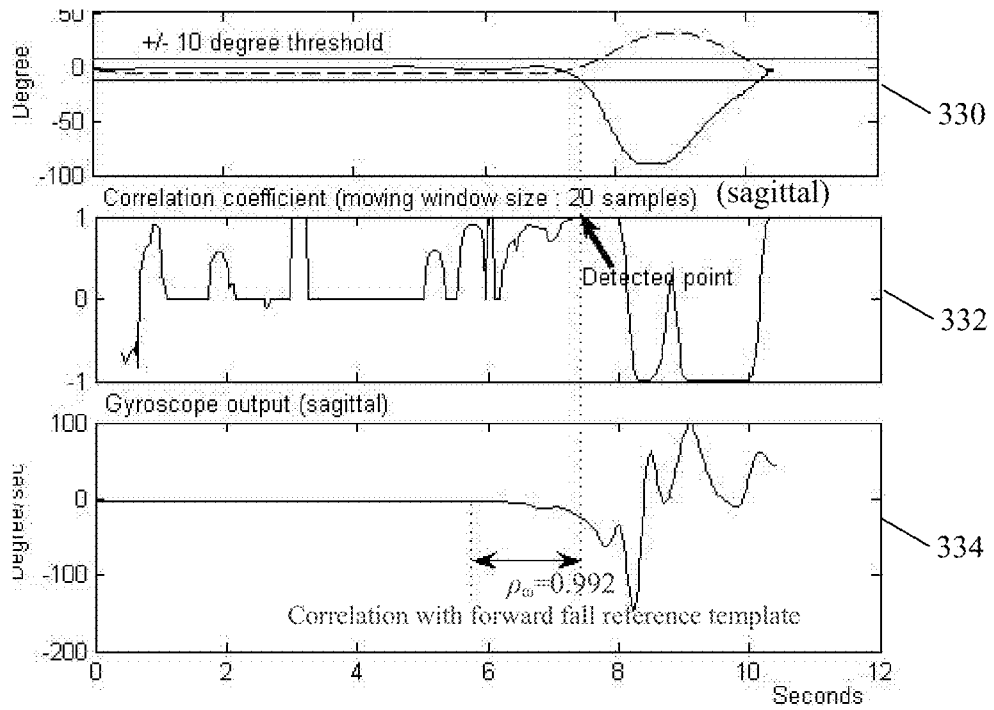
Figure 3:
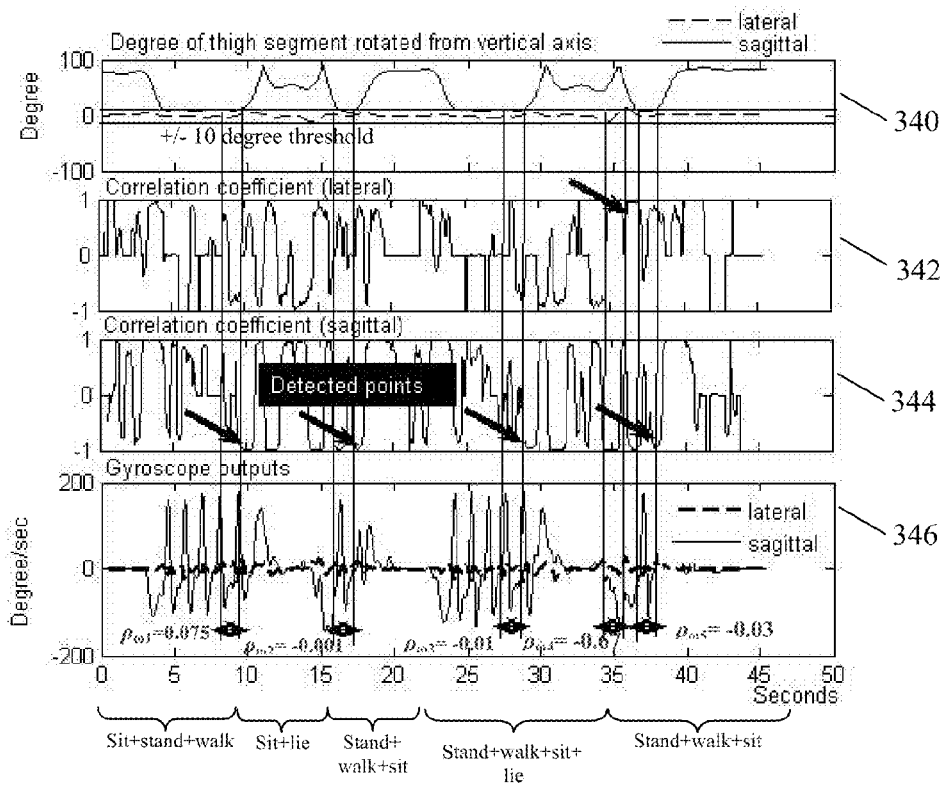
FIGS. 3e and f show measurement graphs for normal activities.
FIG. 3g shows plots of the eighty samples long reference templates for falls, used in the example embodiment.

FIG. 3d shows thigh angle rotation from vertical axis (graph 330), the correlation coefficient of the angle data segments from TS and WS (graph 332), the gyroscope output (graph 334), and the correlation coefficient (indicated in graph 334) of the band pass filtered output of an eighty samples long segment and its corresponding reference template for a simulated left side fall for a simulated forward fall. High correlation coefficients of $\rho_{deg}$ and $\rho_{deg}$ can be seen in the fall activity.

FIG. 3g shows plots of the eighty samples long reference templates for left fall (curve 360), right fall (curve 362), back fall (curve 364) and front fall (curve 366), used in the example embodiment.

FIG. 3e shows thigh angle rotation from vertical axis (graph 340), the lateral correlation coefficient of angle data segments from TS and WS (graphs 342 and 344), and the gyroscope output (graph 346) and correlation coefficient (indicated in graph 346) of the band pass filtered output of 80 samples long segments and their corresponding reference templates for normal activities. $\rho_\omega$ was found to be low in normal activities albeit the corresponding $\rho_{deg}$, normally low, are occasionally high. As the thigh angle is 0 degree for standing posture and 90 degree for sitting posture, the sagittal angle curve is swinging between 0 and 90 degree (curve 351 in graph 350). But stand-sit transitions, similar to backward falls, were successfully rejected in the example embodiment using the two correlation coefficients, $\rho_{deg}$ and $\rho_\omega$.

Figure 3F:
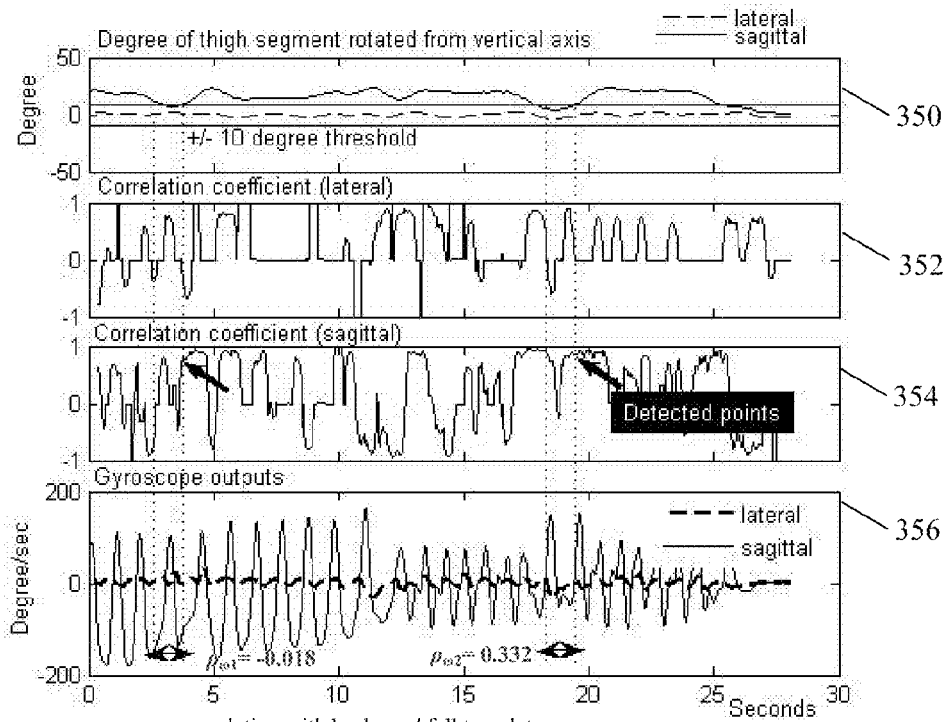

FIG. 3f shows thigh angle rotation from vertical axis (graph 350), the lateral correlation coefficient of angle data segments from TS and WS (graphs 352 and 354), and the gyroscope output (graph 356) and correlation coefficient (indicated in graph 356) of the band pass filtered output of 80 samples long segments and their corresponding reference templates for ascending and descending stairs. $\rho_\omega$ was found to be low in ascending and descending stairs albeit the corresponding $\rho_{deg}$, normally low, are occasionally high.

Only two in thirty seven front falls during confidential simulations were not detected and resulted in 94.6 per cent sensitivity for forward fall, and 100 per cent sensitivity for other falls with no false alarms, where sensitivity is computed as activities detected (35 forward falls) divided by total activities (37 forward falls used in validation).

Figure 4:
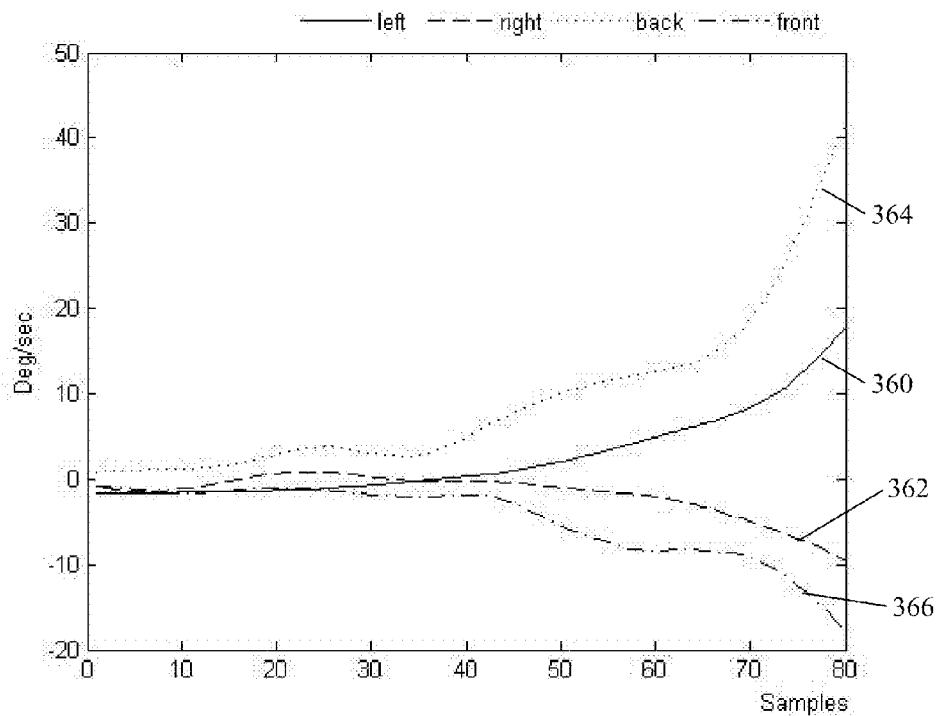
FIG. 4 shows graphs of detection points for the method and system for fall-onset detection according to the-example embodiment.
Figure 4:
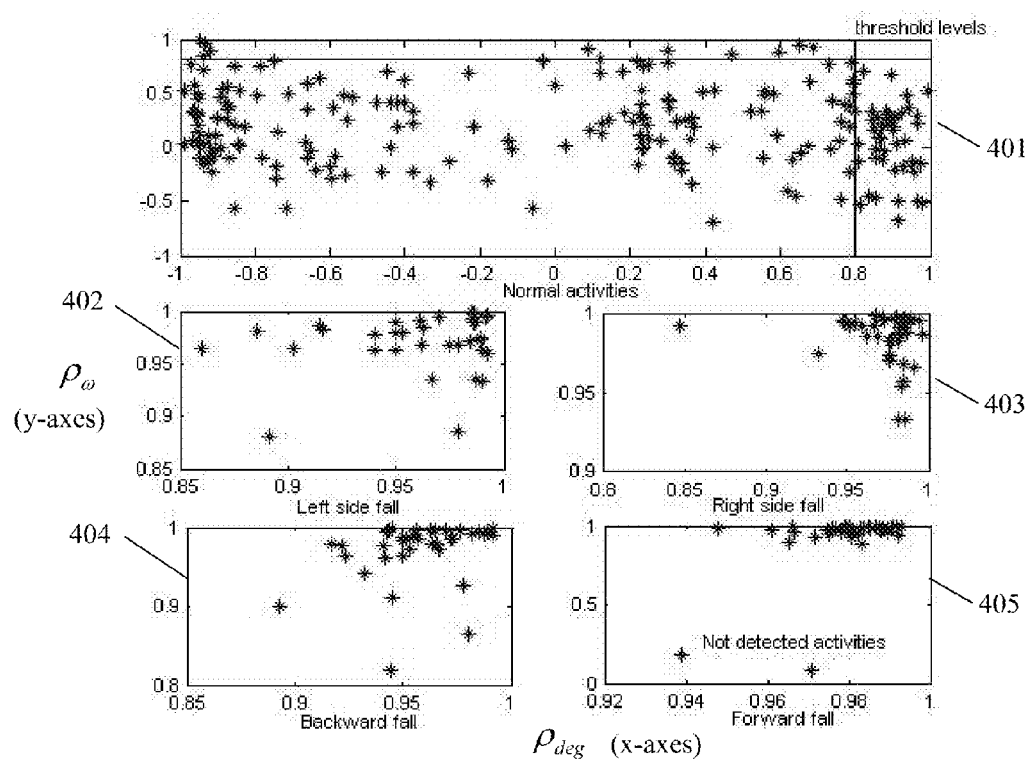

FIG. 4 shows the correlation coefficient relationships of falls and normal activities in the example embodiment, where $\rho_{deg}$ is plotted on the y-axis, and $\rho_\omega$ is plotted on the x-axis in the respective graphs 401 to 405. 216 data of normal activities were plotted which was the number of detected points using ±10 degree threshold levels in the confidential simulations.

As can be seen from graph 401, none of the normal activities detected points were located within the area 410 of $\rho_{deg}$ and $\rho_\omega$ both being above their respective threshold levels. In contrast, for each of the different fall scenarios (graphs 402 to 405), all simulated falls were identified, as indicated by the detected points in the respective graphs, with the exception of two activities for forward fall (compare graph 405). For the two un-detected activities, it was found that in the confidential simulations, the test person was kneeling down first before they released their bodies onto a fall-mattress in the forward direction. As would be appreciated, in kneeling down, the thigh goes backward while the waist level is moving forward and thus the correlation coefficients of $\rho_\omega$ become lower than the threshold value. However, as will also be appreciated, this direction of fall is not typical of unconscious faint fall of the type that typically causes major injuries.

Figure 5:
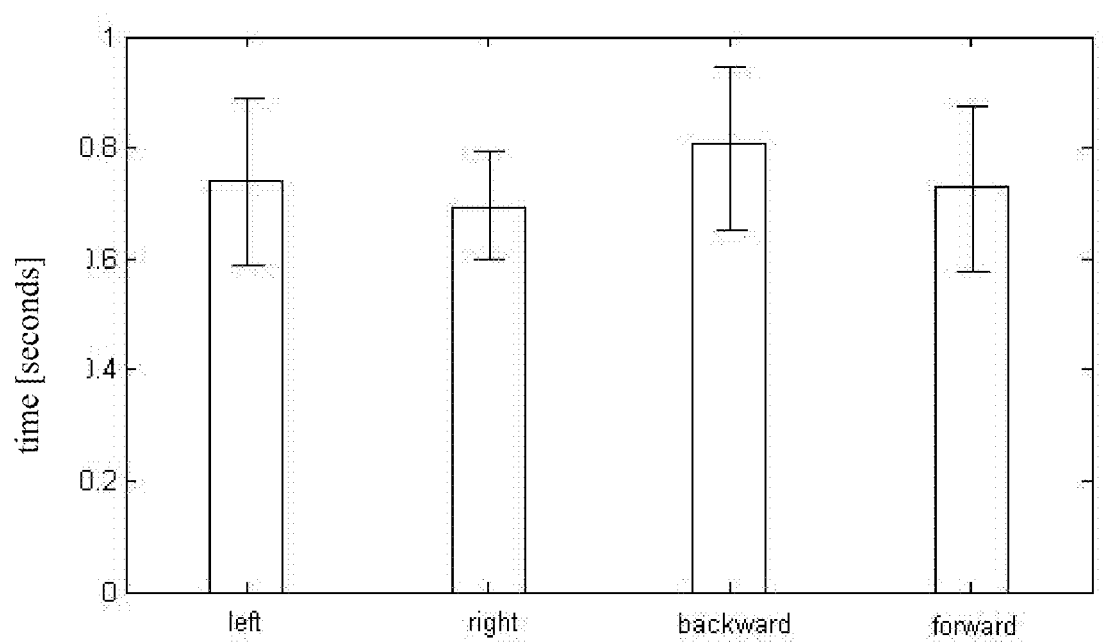
FIG. 5 shows a graph of means and standard deviations of lead time for fall detection for the method and system for fall-onset detection according to the example embodiment.

Means and standard deviations of lead times of falls are shown in FIG. 5. The method of lead time measurement was based on the time difference between the time of the detected point, and the maximum gyroscope output for the relevant fall situation (compare e.g. the lead time indicated at arrow 321 in graph 324 in FIG. 3c).

Figure 6:
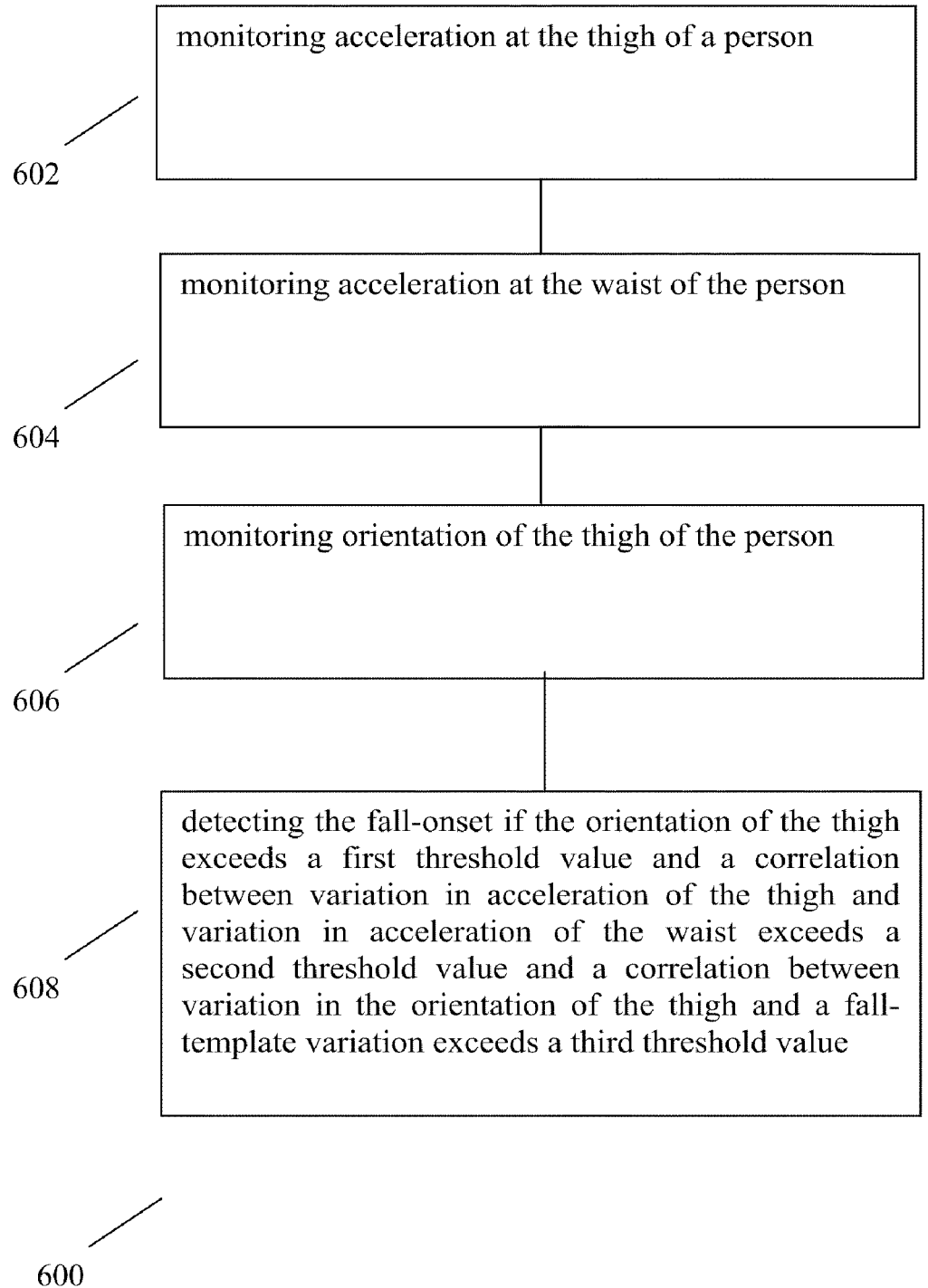
FIG. 6 shows a flowchart 600 illustrating a method of fall-onset detection according to an example embodiment.

FIG. 6 shows a flowchart 600 illustrating a method of fall-onset detection according to an example embodiment. At step 602, acceleration at the thigh of a person is monitored. At step 604, acceleration at the waist of the person is monitored. At step 606, orientation of the thigh of the person is monitored. At step 608, the fall-onset is detected if the orientation of the thigh exceeds a first threshold value and a correlation between variation in acceleration of the thigh and variation in acceleration of the waist exceeds a second threshold value and a correlation between variation in the orientation of the thigh and a fall-template variation exceeds a third threshold value.

Whilst fall risk assessment has been most focused on elderly falls related research work, the described example embodiment is more generally applicable to fall safety in persons of all ages, including in hazardous environments such as construction sites. The described embodiment can activate a feedback system during the lead time, that is the time interval between when the fall is detected and when the subject hits the floor, in preventing faint fall or minimizing the severity of fall related injuries. One non-limiting example of such feedback systems is and inflatable hip protector to cushion the fall prior to impact.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

For example, while example values for the various thresholds and the sample size have been described, it will be appreciated that the present invention is not limited to those specific examples. Rather, other values may be used depending on, for example, different application environments, different measurement equipment, or both.

The invention claimed is:

1. A method of fall-onset detection, the method comprising the steps of:
    providing an accelerometer for monitoring acceleration;
    monitoring acceleration at the thigh of a person;
    monitoring acceleration at the waist of the person;
    monitoring orientation of the thigh of the person; and
    detecting the fall-onset if
        the orientation of the thigh exceeds a first threshold value and
        a correlation between variation in acceleration of the thigh and variation in acceleration of the waist exceeds a second threshold value and
        a correlation between variation in the orientation of the thigh and a fall-template variation exceeds a third threshold value.

2. The method as claimed in claim 1, wherein the first threshold value is about ±10°.

3. The method as claimed in claim 1, wherein the second threshold value is about 0.88.

4. The method as claimed in claim 1, wherein the third threshold value is about 0.8.

5. The method as claimed in claim 4, wherein the acceleration of the waist is monitored three-dimensionally as:
    $\{x_{WS}$: vertical (downward positive); $y_{WS}$: lateral (right positive); $z_{WS}$: sagittal (forward positive)$\}$.

6. The method as claimed in claim 4, wherein the orientation of the thigh is measured two-dimensionally as:
    lateral (left positive) and sagittal (back positive) directions.

7. The method as claimed in claim 1, wherein the acceleration of the thigh is monitored three-dimensionally as:
    $\{x_{TS}$: vertical (downward positive); $y_{TS}$: lateral (right positive); $z_{TS}$: sagittal (forward positive)$\}$.

8. The method as claimed in claim 1, wherein the monitored acceleration of the thigh and waist are transformed into two-dimensional body orientation and the correlation between the variation in acceleration of the thigh and variation in acceleration of the waist is determined with regard to the transformed two-dimensional body orientation.

9. The method as claimed in claim 8, wherein the monitored acceleration of the thigh and waist are transformed into two-dimensional body orientation $\deg_{SAG}$, $\deg_{LAT}$, as:

$$\deg_{SAG} = -a\tan(z_{TSorWS}/x_{TSorWS}) * (180/\text{pi}),$$

$$e = \text{sqrt}(1 - (y_{TSorWS} * y_{TSorWS})), \text{ and}$$

$$\deg_{LAT} = a\tan(y_{TSorWS}/e) * (180/\text{pi}).$$

10. The method as claimed in claim 1, wherein the correlation between variation in acceleration of the thigh and variation in acceleration of the waist is determined over a first data segment of pre-determined sample length.

11. The method as claimed in claim 10, wherein the sample length is about 20.

12. The method as claimed in claim 1, wherein the correlation between variation in the orientation of the thigh and a fall-template variation is determined over a second data segment of pre-determined sample length.

13. The method as claimed in claim 12, wherein the sample length is about 80.

14. The method as claimed in claim 1, further comprising performing a feedback step in response to the fall-onset detection.

15. A system for fall-onset detection, the system comprising:
    a first accelerometer for monitoring acceleration at the thigh of a person;
    a second accelerometer for monitoring acceleration at the waist of the person;
    a gyroscope for monitoring orientation of the thigh of the person; and
    a processor coupled to the first and second accelerometers and to the gyroscope for detecting the fall-onset, the processor being operable to detect the fall-onset based if
        the orientation of the thigh exceeds a first threshold value and
        a correlation between variation in acceleration of the thigh and variation in acceleration of the waist exceeds a second threshold value and
        a correlation between variation in the orientation of the thigh and a fall-template variation exceeds a third threshold value.

* * * * *